United States Patent [19]

Richard

[11] Patent Number: 5,042,508
[45] Date of Patent: Aug. 27, 1991

[54] FRACTURED LIMB STABILIZING DEVICE

[76] Inventor: Patricia A. Richard, 100 Sandpiper Cir., Milford, Conn. 06460

[21] Appl. No.: 574,492

[22] Filed: Aug. 23, 1990

Related U.S. Application Data

[63] Continuation of Ser. No. 425,564, Oct. 23, 1989, abandoned.

[51] Int. Cl.$^5$ ............................................. A61F 5/37
[52] U.S. Cl. ........................................ 128/882; 5/443; 269/328
[58] Field of Search .................... 128/878, 882, 83; 2/266; 269/328, 75; 5/443; 248/118; 197/423, 439; 297/427

[56] References Cited

U.S. PATENT DOCUMENTS

| | | | |
|---|---|---|---|
| 1,429,776 | 9/1922 | Robinson | 248/74.2 |
| 2,522,887 | 9/1950 | Nelson | 5/443 |
| 2,709,435 | 5/1955 | Kress | 5/443 |
| 2,732,269 | 1/1956 | Astroff | 269/328 |
| 2,744,526 | 5/1956 | Saylors | 128/878 |
| 2,850,342 | 9/1958 | Robinson | 5/443 |
| 3,027,895 | 4/1962 | Williams | 128/878 |
| 3,044,797 | 7/1962 | Borland | 5/443 |
| 3,482,566 | 12/1969 | Watkins | 128/882 |
| 3,901,228 | 8/1975 | Brown | 415/194 |
| 3,981,030 | 9/1976 | Turner | 5/443 |
| 4,023,568 | 5/1977 | Murphy | 128/83 |
| 4,090,268 | 5/1978 | Turner | 5/443 |
| 4,169,468 | 10/1979 | Murphy | 128/83 |
| 4,181,297 | 1/1980 | Nichols | 269/328 |
| 4,186,738 | 2/1980 | Schleicher et al. | 128/892 |
| 4,275,472 | 6/1981 | Erck | 5/443 |
| 4,299,213 | 11/1981 | Violet | 128/882 |
| 4,373,709 | 2/1983 | Whitt | 128/882 |
| 4,407,277 | 10/1983 | Ellison | 128/882 |
| 4,428,571 | 1/1984 | Sugerman | 269/328 |
| 4,809,687 | 3/1989 | Allen | 128/84 R |

*Primary Examiner*—Robert A. Hafer
*Assistant Examiner*—Kevin G. Rooney
*Attorney, Agent, or Firm*—Ware, Fressola, Van Der Sluys & Adolphson

[57] ABSTRACT

A limb positioning and stabilizing device provides, in a unitary construction, an arcuate limb engaging element, which, when forced open, will return to its original shape when the force is no longer applied, for embracing an injured limb, and also provides a wide transverse support base, which is integral with the limb engaging element, for bracing the limb engaging element when the device is in operation. The device further provides a padded inner lining for protecting the injured limb and an attachment means for attaching a plurality of the devices in parallel for use with longer limbs.

14 Claims, 2 Drawing Sheets

FRACTURED LIMB STABILIZING DEVICE

This is a continuation of copending application Ser. No. 07/425,564 filed on 10/23/89 now abandoned.

BACKGROUND OF THE INVENTION

1. Field of the Invention

The present invention relates to positioning and stabilizing devices for fractured limbs, and, more particularly, to a portable brace used for stabilizing an injured extremity to promote healing

2. Background of the Invention

In the field of orthopedic surgery, and especially those fields dealing specifically with injuries to extremities (i.e., fractured bones in the legs or arms, etc.), there is a need for stabilization of the injured extremity for healing purposes. Because nerves, blood vessels, connective tissue and muscles lie in close proximity to bones, these structures can be injured by the jagged ends of the bones if the bones are broken or fractured. The fractured edges of the broken bone, when torqued, dig into the surrounding tissue structures causing trauma or further injury and pain and, likewise, further edema (swelling) and hematoma (blood clotting).

To treat fractured bones after reduction or setting of the fracture, a cast is normally applied to the fractured extremity as a means of stabilizing the fractured ends so that new bone tissue can eventually bridge between the ends creating a united bone. In the meantime, a fracture heals slowly, going through a process of hematoma (clot) formation followed by granulation tissue, the differentiation of fibrous tissue into fibrocartilage and the growth of bone cells into this tissue type, calcification, and remodeling of the bone until a firm mature bone is formed.

However, the study of anatomy of the musculoskeletal system shows that the entire system is connected. Muscles attach under the cast. Thus, varying degrees of internal and external rotation are still possible within a cast extremity. Thus, there is a need to stabilize the cast extremity in order to maintain it in a neutral position.

As shown in FIG. 3, when the cast leg 26 is resting on a flat surface 30, there is an inherent tendency for the thigh to externally rotate slightly. The movement, indicated by arrows 31, is further aggravated by the intrinsic weight of the cast and the ovoid-like shape of the leg. The extra degree of rotation of the cast portion of the extremity may pull the two fractured bone pieces out of alignment. This is especially painful during the early stages of healing when there is much edema and hematoma impinging on the nerves.

Furthermore, with time, muscles which are not actively employed in the manner they normally are employed, tend to atrophy. This atrophy or shrinking of muscles enclosed within a cast creates a space between the outer skin surface and inner cast surface permitting an additional risk of twisting of the extremity within the cast.

DESCRIPTION OF THE PRIOR ART

A number of limb holding and supporting devices have heretofore been developed to stabilize an extremity in a single position for various purposes including stabilizing a limb for a surgical operation or an X-ray, supporting and maintaining limbs (i.e., legs) in the proper orientation for an even tan, as well as positioning and comfortably supporting cast limbs for patients at rest.

The foot restraining device of Watkins U.S. Pat. No. 3,482,566 and the foot support of Turner U.S. Pat. No. 4,090,268 teach the use of a saddle-like apparatus, positioned at the feet or heels of a sunbather, to support the sunbather's feet, and thus position his/her legs in an upright situation. This guarantees an even tan without risking overexposure to the sun of the sensitive inner thigh.

Many different devices have been developed to position and stabilize a human limb for surgical operations, examinations, X-ray photography, or other medical procedures. Astroff U.S. Pat. No. 2,732,269 shows the use of a U-shaped brace set upon a wide H-shaped supporting base connected by a long, telescopically adjustable upright leg to support a patient's arms or leg during surgical operations. The leg is pivotable at its junction with the base. Additionally, the brace is pivotable about its junction with the leg. In Robinson. U.S. Pat. No. 2,850,342, a U-shaped limb engaging element is supported by a portable pedestal support, which is truncated-pyramid shaped. The limb engaging element, which is elevated some distance, can rotate on top of the pedestal support. This device is utilized for limb amputational surgery. Nichols. U.S. Pat. No. 4,181,297, teaches the use of a plurality of mechanisms used in combination to position, support, and secure to an examining table a human limb for examination or treatment. Violet, U.S. Pat. No. 4,299,213 also teaches the use of a table-mounted leg positioning device utilized for limb surgery. This device uses an inflatable limb engaging element. Finally, in Sugarman, U.S. Pat. No. 4,428,571, two limb-grasping elements are pivotably connected to adjustably position a leg for surgery.

In addition to positioning devices used as a surgical aid, devices have been developed to stabilize injured limbs for therapeutic purposes. Brown, U. S. Pat. No. 3,901,228, provides a boot-like body to be wrapped around a patient's ankle and foot to maintain the foot and, thus, the leg in an upright position. In Murphy, U.S. Pat. No. 4,023,568, the cast positioning device comprises an eye member, through which a cord can be run, attached to a body portion which becomes embedded in the wet cast plaster. Through the use of the cord, the cast (on a leg) can be positioned. Furthermore, Murphy U.S. Pat. No. 4,169,468 shows a similar concept in which multiple eyes are embedded in the wet cast plaster to form a multiple positioning cast support device. Schleicher, U.S. Pat. No. 4,186,738, further develops an idea used in Brown. U.S. Pat. No. 3,901,228, by employing a heel supporting and protective boot to hold a bed patient's foot upright. Finally, Allen, U.S. Pat. No. 4,809,687, discloses a boot-shaped cradle supported by an arm attached to a table surface and adjustable straps.

Additional supports have heretofore been developed for uses other than for limb support (i.e., supports for pipes, cables, electric conductors, etc.). Robinson, U.S. Pat. No 1,429,776, illustrates an upstanding support of unitary structure for supporting pipes, cables and the like. The support is formed from a tube, which is flattened, cut, and bent, and comprises a cable-engaging unit supported by a vertical elevating leg and a base.

Though these references show many configurations and uses of limb supporting devices, none disclose a portable, adjustable, as well as economical and simple-to-use leg support to maintain a cast leg in an upright position, as the present invention does. This invention incorporates a simple unitary structure comprising a slightly flexible, U-shaped cast limb engager integrally joined to a long and thin supporting base. The flexible engager utilizes partial ring-like arms to hold the cast or limb while providing flexibility to accept different sized casts/limbs. Additionally, the limb engaging element is integral with its long, thin transverse base thus providing the stability necessary for an effective and desirable limb immobilizer. Its unitary construction allows for easy and economical manufacture, as well as for simple and convenient use. A padded lining along the inner circumference of the limb engager provides comfort to the user while preventing damage to the cast or limb. Finally, a plurality of these limb immobilizers may be utilized in combination to accommodate limbs of different lengths.

This combination of useful features of the limb immobilizer is not believed to be disclosed or suggested by any of the prior art patents. The preferred embodiment of the present invention is for use on a bed or other resting surfaces for stabilizing an injured limb during therapeutic rehabilitation. It is easily utilized by the patient and thus eliminates the need for medical assistance. Its small size and light weight make the invention portable and convenient.

The present inventor has thus discovered that a wide range of requirements, as well as conveniences, for a limb immobilizer can be met by providing a flexible ring-like embracing device which is integral with its wide transverse base. Particularly when used by patients rehabilitating at home who do not have access to constant medical assistance, these convenient and portable devices are useful to those patients who need an effective and comfortable limb immobilizer and desire an immobilizer which is portable yet economical and easy to use.

Accordingly, a principal object of the invention is to provide a versatile and effective limb immobilizing device affording the conveniences of flexibility for accepting various sized limbs and allowing easy installation of a cast, and portability for use on different resting surfaces.

A further object of the invention is to provide the limb immobilizer with an attachment means allowing a plurality of the devices to be utilized in combination to effectively stabilize longer limbs.

Another object of the invention is to provide the limb engaging element of the device with a padded soft inner lining to reduce pressure points and prevent irritation of the skin or damage to the cast.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

For a fuller understanding of the nature and objects of the invention, reference should be had to the following detailed description taken in connection with the accompanying drawings, in which:

THE DRAWINGS

Figure 4:
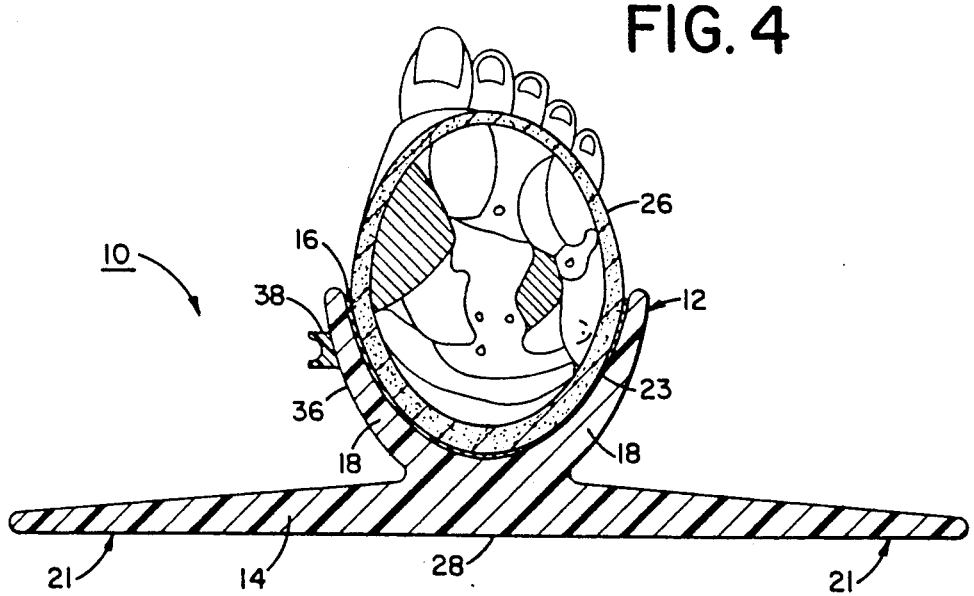
FIG. 4 is a side elevational view of the same device shown in cross-section taken along plane 4—4 shown in FIG. 2.
Figure 5:
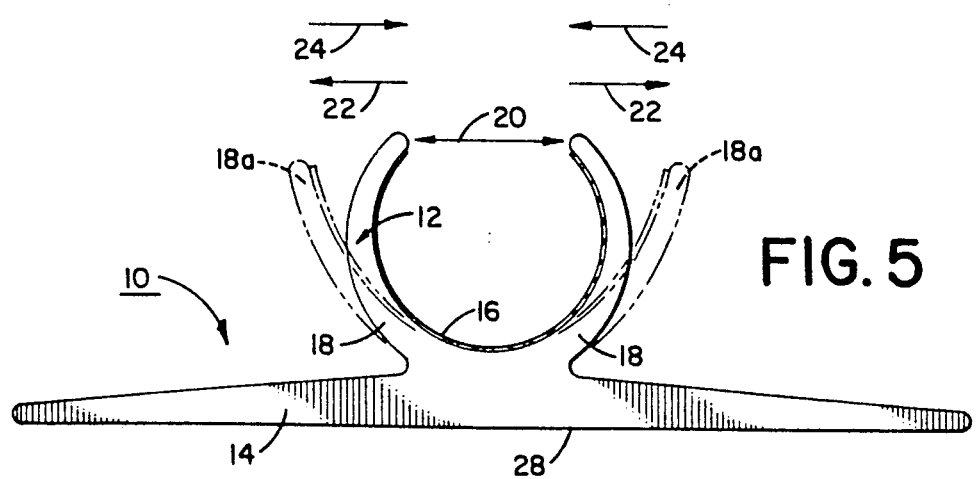

FIG. 4 showing the internal structure of the human leg;

FIG. 5 is a perspective view of the same device showing the flexibility of a limb embracing member of the device.

Figure 1:
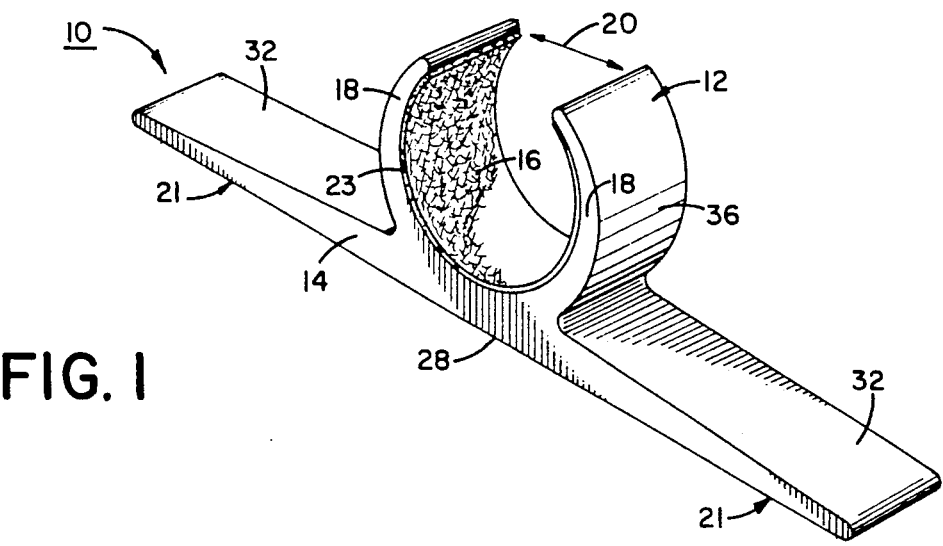
FIG. 1 is a perspective view of a limb stabilizing device of the present invention.

As best seen in FIG. 1, the limb immobilizing device, indicated generally by the numeral 10, which is constructed of a single piece of plastic or another flexible material, incorporates three cooperating parts, a U-shaped limb engaging element, indicated generally by the numeral 12, a support base 14, and a padded lining 16.

The limb engaging element 12 is a circular sector or U-shaped component employed to grasp the limb or cast to be immobilized. It is comprised of two flexible arms 18 which are arc-shaped and are joined together at the support base 14 thus forming the engaging element circular sector shape. The distal ends of arms 18 are not joined opposite the support base 14, leaving a gap 20 between the two arms 18 and thus an access to the embracing element 12 for a limb or cast to be inserted.

The limb engaging element 12, as well as the entire immobilizing device 10, is constructed of a semi-flexible plastic or other suitable resilient material that will have the flexibility to bend when an appropriate force is applied but also have the resiliency to recover its original shape when the force is no longer applied. Alternative materials for the device 10 include aluminum and elastomer as well as other similar materials. This characteristic of the device 10 and the material used is depicted in FIG. 5, where the arms 18 are shown resiliently separated in dashed lines 18a to accept a cast. This construction allows the engaging arms 18 to be spread away from one another, with an expansive force 22, thus widening the gap 20 to permit the insertion of the limb or cast to be immobilized, and, when the expansive force 22 is removed, the engaging arms 18, utilizing their own inherent retractive force 24, are able to return to their approximate original configuration by conforming around the inserted cast limb 26. The limb immobilizing device 10 conformed around an inserted cast 26 is shown in cross-section in FIG. 4.

As can be seen in FIG. 1, an inner element wall 23, which preferably encompasses the entire inner circumference of the limb engaging element 12, is lined with a soft padded lining 16. The padded lining 16 reduces pressure points and prevents irritation of the skin or damaging of the cast 26 when the limb engaging element 12 has embraced the limb or cast as shown in FIG. 4.

The cross-sectional area of the limb engaging element 12 may be varied for different limb embracing devices 10 by varying the lengths of the flexible arms 18 and their corresponding width, thickness and radii of curvature. Variations in the radii of curvature and lengths of the arms 18 will correspondingly vary the internal diameter of the limb engaging element 12 and, thus will allow different sized limb immobilizing devices to be employed for different sized casts and/or limbs. Various sized limb immobilizing devices 10 are shown in operation in FIG. 2.

Figure 2:
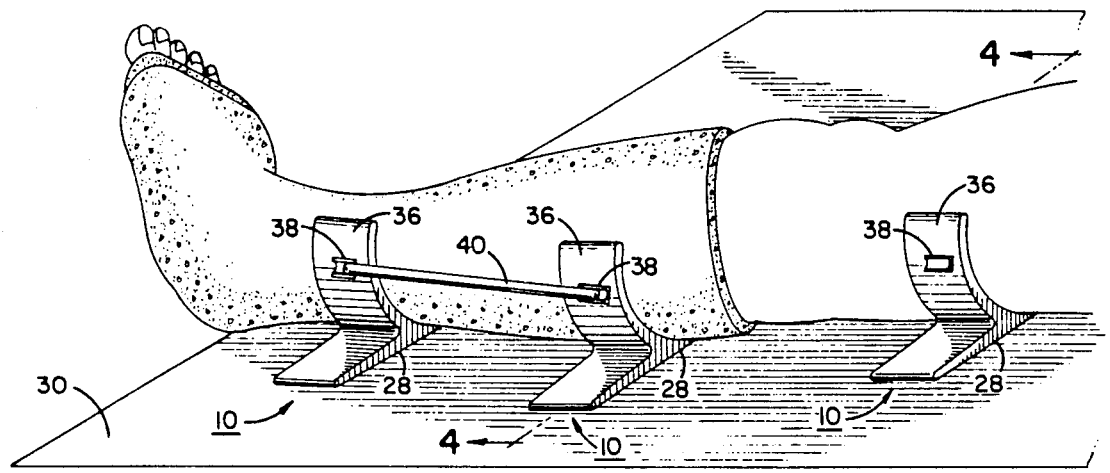
FIG. 2 is a perspective view of three limb immobilizing devices of the present invention, shown in an operative condition immobilizing a cast leg.
Figure 3:
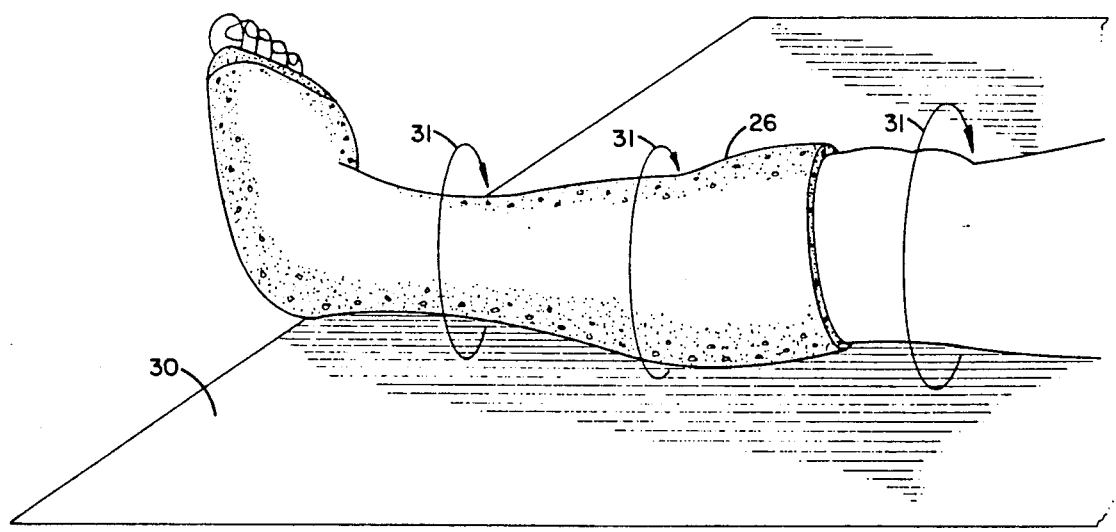
FIG. 3 is a perspective view of a cast leg showing a natural tendency of rotation.

As shown in FIG. 1, the support base 14 incorporates two lateral support legs, indicated generally by the numeral 21, extending outwardly in an opposite direction from each other forming a long flat portion, or base 14, joined to the limb engaging element 12 at the juncture of the two engaging arms 18. Base 14 incorporates a flat bottom surface 28, which, when in operation, forms contact with a resting surface 30, as shown in FIG. 2. As shown in FIGURE 1, the support base 14 also utilizes two smooth top surfaces 32 which extend from each side of the limb engaging element 12/support base 14 junction outwardly to the support base bottom surface 28. Both support base top surfaces 32, beginning at the element 12/base 14 junction, incline at a slight angle as they extend to the base bottom surface 28. Smooth surfaces 32 are comfortably handled, and avoid snagging hands or fabrics.

The support base 14 performs the function of stabilizing the limb engaging element 12 and, therefore, it is long in comparison to the diameter of the engaging element 12. The preferred embodiment shows a three to one support base length to engaging element diameter ratio, although this ratio, of course, may be varied and the limb immobilizing device will remain functionally equivalent. Furthermore, because the support base 14 must stabilize a cast leg inserted in the limb engaging element 12, its thickness from top surface 32 to bottom surface 28 must be substantial enough to support a reasonable amount of torque applied from a cast leg 26 rolling action.

Because the support base 14 is transversely positioned tangentially to and is integral with the limb engaging element 12, the base 14 provides a maximum amount of stability to prevent a rolling action of the device 10 and, thus, the cast leg 26. Furthermore, because the base 14 has a small upward elevation, the device 10 ultimately is provided with a low center of gravity and a short moment arm. The combination of these characteristics results in a maximally stable limb immobilizing device 10.

Finally, as shown in FIG. 4, on the outer circumference of the limb engaging device 12, that is, on an outer surface 36 of one engaging arm 18, an attachment element 38 may be utilized, such as a plug-and-socket or a spring detent. As illustrated in FIG. 2, employing the attachment element 38 in combination with a mating attachment rod 40 of pre-selected length allows the utilization of a spaced apart plurality of limb immobilizing devices 10 in parallel for longer limbs.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A limb positioning and stabilizing device comprising:

A. a limb engaging element of resilient material for embracing an injured limb incorporating two flexible limb-engaging arms, forming a generally arcuate structure having an internal diameter substantially matching that of the limb, which arms, when forced apart, by a spreading force, will return to their original shape when said force is no longer applied; and wherein an outer surface of one of said arms of said limb engaging element is provided with attachment means for attaching a plurality of said positioning and stabilizing devices in substantially parallel spaced locations, and B. a transverse support base unitary with and bracing said limb engaging element, said support base being tangential to and integral with said arcuate limb engaging element, said support base having a small upward elevation and a length significantly greater than the diameter of said limb engaging element and incorporating two legs which protrude transversely in opposite lateral directions in a parallel plane with said limb engaging element.

2. A limb positioning and stabilizing device comprising:

A. a limb engaging element of resilient material for embracing an injured limb incorporating two flexible concave limb-engaging arms extending laterally from a central portion of said element, curving upward concavely facing each other and forming a generally arcuate structure having an internal diameter substantially matching that of the limb, which arms, when forced apart by a spreading force, will return to their original shape when said force is no longer applied, said limb engaging element having an inner surface covered with a padded lining for contacting the injured limb and B. a substantially flat-bottomed transverse support base unitary with said central portion and bracing said limb engaging element, said support base being tangential to and integral with said arcuate limb engaging element positioning said central portion at a small upward elevation above said flat bottom and said support base having a lateral transverse length at least eight times greater than said elevation of said limb engaging element and incorporating two legs which protrude transversely in opposite lateral directions in a parallel plane with said limb engaging element, whereby said injured limb is supported at said elevation above a supporting surface and is stabilized against rotational movement.

3. The positioning and stabilizing device defined in claim 2 wherein said limb engaging element is U-shaped and is joined to said support base at a juncture of said two limb-engaging arms.

4. The positioning and stabilizing device defined in claim 2 wherein said support base has a transverse length substantially equal to three times the diameter of said limb engaging element.

5. The positioning and stabilizing device defined in claim 2 wherein said resilient material is plastic.

6. The positioning and stabilizing device defined in claim 2 wherein said resilient material is aluminum.

7. The positioning and stabilizing device defined in claim 2 wherein said resilient material is elastomer.

8. A limb positioning and stabilizing device comprising:

A. a limb engaging element of resilient material for embracing an injured limb incorporating two flexible limb-engaging arms forming a generally arcuate structure having an internal diameter substantially matching that of the limb, which arms, when forced apart by a spreading force, will return to their original shape when said force is no longer applied, an outer surface of one of said arms being provided with attachment means for attaching a plurality of said positioning and stabilizing devices in substantially parallel spaced locations; and B. a transverse support base unitary with and bracing said limb engaging element, said support base being tangential to and integral with said arcuate limb engaging element, said support base having a small upward elevation and a length significantly greater than the diameter of said limb engaging element, and incorporating two legs which protrude transversely in opposite lateral directions in a parallel plane with said limb engaging element.

9. The positioning and stabilizing device defined in claim 8 wherein an inner surface of said limb engaging element is covered with a padded lining for contacting an injured limb.

10. The positioning and stabilizing device defined in claim 8 wherein said limb engaging element is U-shaped and is joined to said support base at a juncture of said two limb-engaging arms.

11. The positioning and stabilizing device defined in claim 8 wherein said support base has a transverse length substantially equal to three times the diameter of said limb engaging element.

12. The positioning and stabilizing device defined in claim 8 wherein said resilient material is plastic.

13. The positioning and stabilizing device defined in claim 8 wherein said resilient material is aluminum.

14. The positioning and stabilizing device defined in claim 8 wherein said resilient material is elastomer.

* * * * *